Figure 1:
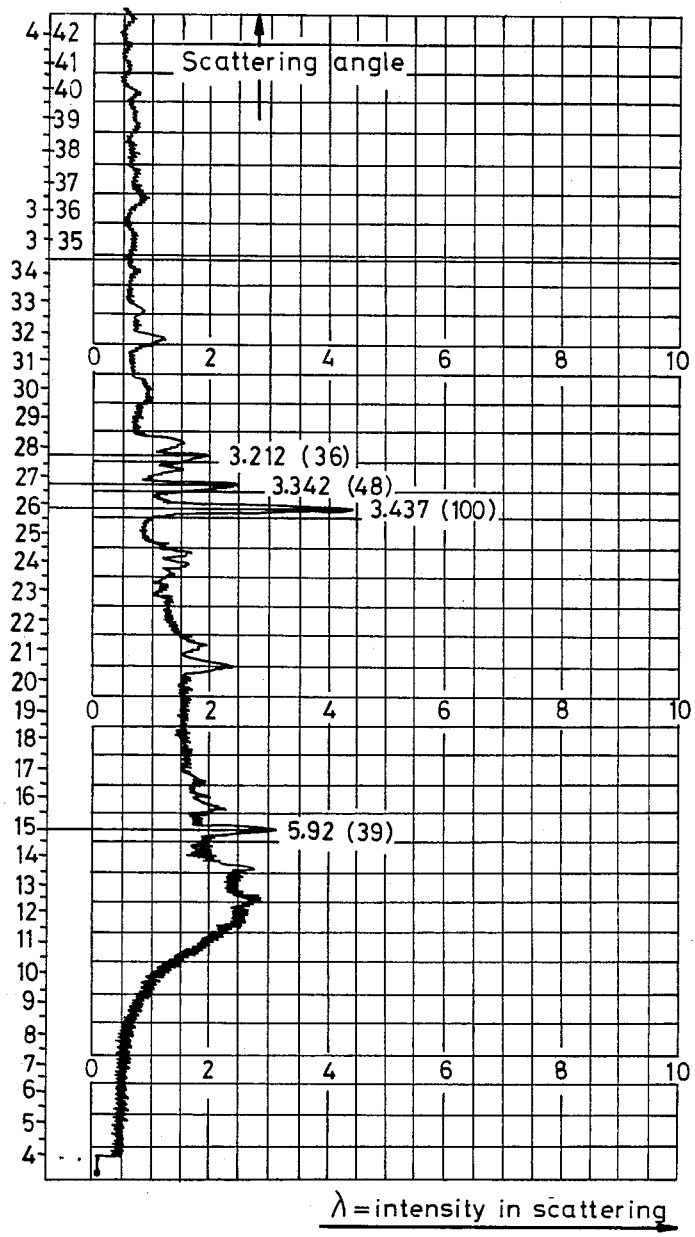

United States Patent [19]

Harsányi et al.

[11] Patent Number: 4,579,954

[45] Date of Patent: Apr. 1, 1986

[54] CIMETIDINE MONOHYDRATE

[75] Inventors: Kálmán Harsányi; György Domány, both of Budapest; Oszkár Fuchs, Dunakesz; Lajos Toldy, Budapest; György Fekete, Budapest; Endre Kasztreiner, Budapest; Béla Hegedüs, Budapest; Ferenc Mórász, Budapest; András Radó, Budapest; Tibor Láng, Budapest; Árpád Lázár, Budapest; Éva Csongor, Budapest; Tibor Balogh, Budapest; János Borvendég, Budapest; József Reiter, Budapest; Tibor Somogyi, Budapest; Margit Bidló née Iglóy, Budapest, all of Hungary

[73] Assignee: Richter Gedeon Vegyészeti Gyár Rt., Budapest, Hungary

[21] Appl. No.: 604,385

[22] Filed: Apr. 27, 1984

Related U.S. Application Data

[63] Continuation of Ser. No. 391,852, Jun. 24, 1982, abandoned.

[30] Foreign Application Priority Data

Jun. 26, 1981 [HU] Hungary ............... 1877/81

[51] Int. Cl.$^4$ ........................... C07D 233/64
[52] U.S. Cl. ................................... 548/342
[58] Field of Search ......................... 548/342

[56] References Cited

FOREIGN PATENT DOCUMENTS 1096387 2/1981 Canada ............................. 548/342

OTHER PUBLICATIONS

Prodic-Kojic, B., et al., *Gazz, Chim. Ital.*, 109, 535 (1979).
Prodic-Kojic, B., et al., *Acta Cryst.* (1980), B36, 1223-1225.

*Primary Examiner*—Richard A. Schwartz
*Attorney, Agent, or Firm*—Keil & Weinkauf

[57] ABSTRACT

The invention relates to the new monohydrate of N-methyl-N'-{2-[(5-methylimidazol-4-yl)-methylthio]-ethyl}-N''-cyanoguanidine (cimetidine), a histamine-$H_2$ receptor antagonist which is called N-methyl-N'-{2-[(5-methylimidazol-4-yl)-methylthio]-ethyl}-N''-cyanoguanidine H (cimetidine H) as well as to a process for the preparation of same, which comprises pouring a hot, homogeneous aqueous solution of N-methyl-N'-{2-[(5-methylimidazol-4-yl)-methylthio]-ethyl}-N''-cyanoguanidine, optionally containing also methylamine, onto ice and separating the N-methyl-N'-{2-[(5-methylimidazol-4-yl)-methylthio]-ethyl}-N''-cyanoguanidine monohydrate.

1 Claim, 2 Drawing Figures

CIMETIDINE MONOHYDRATE

This is a continuation of application Ser. No. 391,852 filed June 24, 1982, now abandoned.

This invention relates to the new monohydrate of N-methyl-N'-{2-[(5-methylimidazol-4-yl)-methylthio]-}ethyl-N''-cyanoguanidine (cimetidine), a histamine H-2 receptor antagonist, as well as to a process for preparing same. In this description, this new monohydrate is named N-methyl-N'-{2-[(5-methylimidazol-4-yl)-methylthio]-ethyl}-N'''-cyanoguanidine H (cimetidine H).

Several modifications of N-methyl-N'-{2-[(5-methylimidazol-4-yl)-methylthio]-ethyl}-N''-cyanoguanidine have been described in the literature. According to the published German patent application No. 2,742,531 the modification A, which is most useful for pharmaceutical purposes, is formed by crystallization from anhydrous media, while modification B or C, respectively, separates from a solvent containing water.

Similar statements are contained in another publication [Gazz. Chim. Ital. 109, 535/1979]. The main conclusion of the latter is that the separation of the individual modifications from an aqueous medium is accidental and cannot be controlled.

From the processes known for the preparation of N-methyl-N'-{2-[(5-methylimidazol-4-yl)-methylthio]-ethyl}-N''-cyanoguanidine, those described in the Belgian patent No. 804,144 have practical importance. These are as follows:

(a) the reaction ethanolic methylamine of N-cyano-N'-{2-[(5-methylimidazol-4-yl)-methylthio]-ethyl}-S-methylisothiourea;

(b) the reaction of 4-[2-(aminomethyl)-thiomethyl]-5-methyl-imidazole with N-cyano-N',S-dimethylisothiourea in acetonitrile by boiling for a long time;

(c) the reaction of N-methyl-N'-{2-[(5-methylimidazol-4-yl)-methylthio]-ethyl}-thiourea with lead cyanamide in a mixture of dimethylformamide and acetonitrile.

All these processes are carried out in anhydrous media. According to the process (b), the product is obtained with a yield of only 20% after purifying with column chromatography [J. Med. Chem. 20, 901/1977]. The yield of the process (c) (i.e. 40%) also falls below the effectivity required in the last step of a reaction sequence. Another disadvantage of process (c) is the use of a lead reagent.

Although process (a) seems to be problem-free concerning the yield, the carrying out of the reaction and working up of the reaction mixture is rather problematic. According to the Belgian Pat. No. 804,144 [Example 1 (c) (ii)], the reaction takes place at room temperature with a large excess of methylamine in ethanol, the mixture is then evaporated and the residue recrystallized from a mixture of isopropanol and petroleum ether. The inconveniences of this method can be summarized as follows. Methyl mercaptan, arising from the condensation reaction, does not pass out from the system in the course of the reaction carried out at room temperature and as a consequence, the simultaneous leaving of both gases proceeds during evaporation so violently that the binding of these gases cannot be solved. N-methyl-N'-{2-[(5-methylimidazol-4-yl)-methylthio]-ethyl}-N''-cyanoguanidine as the reaction product appears as an evaporation residue containing all contaminations and side products. These cannot be removed in the way described in the Example cited from the Belgian Pat. No. 804,144; thus, the recrystallisation does not result in a product of the required quality.

When preparing N-methyl-N'-{2-[(5-methylimidazol-4-yl)-methylthio]-ethyl}-N''-cyanoguanidine in anhydrous media, the recrystallisation and purification to a certain but not satisfying degree of the compound can be solved by the recrystallisation from an anhydrous organic solvent. This leads to N-methyl-N'-{2-[(5-methylimidazol-4-yl)-methylthio]-ethyl}-N''-cyanoguanidine A which is the most useful modification for pharmaceutical purposes.

During our experiments aimed to improve the chemical preparation of N-methyl-N'-{2-[(5-methylimidazol-4-yl)-methylthio]-ethyl}-N''-cyanoguanidine, it was found that in case of the reaction of N-cyano-N'-{2-[(5-methylimidazol-4-yl)-methylthio]-ethyl}-S-methylisothiourea hydrate (prepared by the method disclosed in Hungarian patent application Ser. No. 899/80) with methyl amine in aqueous media, temperature conditions could be found under which the evolution of methyl mercaptan became smooth; thus, the destruction (annihilation) of same by chemical transformation (burning, oxidation with hypochlorite) could be accomplished more favourably in comparison to the abrupt gas evolution. Namely, the leaving of methyl mercaptan is retarded by methylamine (because of a loose salt formation) at or even above room temperature, while on heating in ethanolic media the methylamine reactant also steps out to a significant extent. On the contrary, when an aqueous medium is used, methyl mercaptan can be eliminated at temperatures (at about 50°–60° C.) far below the boiling point. Thus, methylamine can be used in a lower excess, i.e. more economically: 2 to 5 moles of it are satisfying for the rapid and complete transformation, as opposed to the 10 moles required according to the literature.

The advantages of the process carried out in an aqueous medium concern not only the safety and protection of the environment. Additional advantages are the decrease in the amount of methylamine used and the fact that the N-methyl-N'-{2-[(5-methylimidazol-4-yl)-methylthio]-ethyl}-N''-cyanoguanidine obtained is purer.

Namely, S,S'-bis-[2-(N-cyano-N'-methyl)-guanidino-ethyl-disulphide appears as a side product in the reaction. The preparation of this compound is described in the published German patent application No. 2,944,257 (though with a not satisfying purity). The contamination with disulphide of cisteamine hydrochloride, used for the precursor of the synthesis, is not necessary for the appearance of this compound as impurity. The formation of this substance can be formulated from bis-(2-aminoethyl)-disulphide (contaminating the cisteamine), methyl N-cyanoimidodithiocarbonate and methylamine however, according to our discovery it can also arise from splitting of the C-S bond in the side chain of N-methyl-N'-{2-[(5-methylimidazol-4-yl)-methylthio]-ethyl}-N''-cyanoguanidine. The interchange of various nucleophils in Mannich type compounds is well known. It was found that the above contamination, crystallizing together with the desired product from organic solvents, can be removed even by crystallisation from water, or by a reaction carried out in water and by washing thoroughly out the methylamine with water before drying. On the basis of our experiments, the amount of the contaminating side product considerably increases when the reaction is realized by boiling with the methylamine solution or when the drying is performed in the presence of methylamine. This can be proved by thin layer chromatography on Kieselgel 60F 254 adsorbent, by development with ethyl acetate-acetone-water 5:4:1 system and by evaluation with UV densitometry of the spot appearing with 0.45 $R_f$ value.

The preparation with aqueous methylamine of N-methyl-N'-{2-[(5-methylimidazol-4-yl)-methylthio]-ethyl}-N''-cyanoguanidine is favourable both for carrying out the reaction as well as for obtaining a substance with higher purity. During the practical verification of these advantages, it was aimed to develop a simple process for obtaining N-methyl-N'-{2-[(5-methylimidazol-4-yl)-methylthio]-ethyl}-N''-cyanoguanidine from the aqueous reaction mixture as well as for the preparation of modification A.

It was found that when the homogeneous, aqueous solution containing optionally also methylamine is poured onto ice, the main bulk of the substance crystallizing out is not the amorphous modification B, but a new monohydrate of N-methyl-N'-{2-[(5-methylimidazol-4-yl)-methylthio]-ethyl}-N''-cyanoguanidine, i.e. the modification H. The modification A can be obtained from this modification H by means of a simple recrystallization.

It should be noted that the modification H is slowly transformed to modification A during storage, too. This spontaneous transformation can be accelerated by increasing the temperature.

Thus, this invention relates to the new monohydrate of N-methyl-N'-{2-[(5-methylimidazol-4-yl)-methylthio]-ethyl}-N''-cyanoguanidine as well as to a process for the preparation of same, which comprises pouring a homogeneous aqueous hot solution of N-methyl-N'-{2-[(5-methylimidazol-4-yl)-methylthio]-ethyl}-N''-cyanoguanidine, optionally containing also methylamine, onto ice and separating the obtained N-methyl-N'-{2-[(5-methylimidazol-4-yl)-methylthio]-ethyl}-N''-cyanoguanidine monohydrate from the solution.

Figure 2:
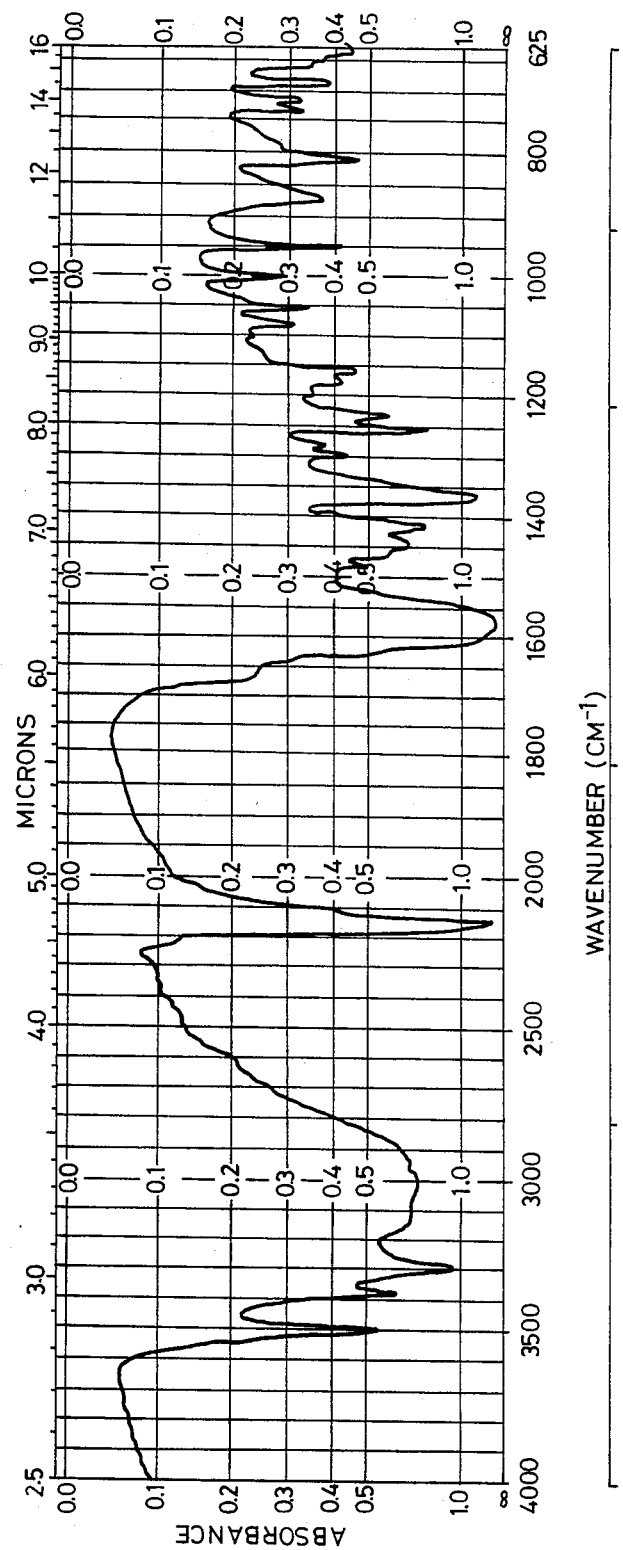

When the solution containing N-methyl-N'-{2-[(5-methylimidazol-4-yl)-methylthio]-ethyl}-N''-cyanoguanidine is cooled relatively slowly, the modification B crystallizes out. When the reaction mixture cools to 20° or a lower temperature without the beginning of crystallization, then the modification H separates from the solution. An effective way for obtaining the modification H consists in pouring a hot aqueous solution of N-methyl-N'-{2-(5-methylimidazol-4-yl)-methylthio]-ethyl}-N''-cyanoguanidine, optionally containing also methylamine, onto ice. The ice is used in an amount approximating the weight of the solution. The solution is poured onto the ice at a considerably high rate. The modification H of N-methyl-N'-{2-[(5-methylimidazol-4-yl)-methylthio]-ethyl}-N''-cyanoguanidine is easily recognized for it forms a well-settling precipitate, which can conveniently be washed out on the filter. The high dry substance content of the modification H gives the possibility of the direct recrystallisation to modification A of the product filtered out, without drying. N-methyl-N'-{2-[(5-methylimidazol-4-yl)-methylthio]-ethyl}-N''-cyanoguanidine H obtained from the solution and containing not more than 30% of water is suitably transformed to the modification A by recrystallisation from an alcohol, favourably from isopropanol. The X-ray diagram and the infrared spectrum of N-methyl-N'-{2-[(5-methylimidazol-4-yl)-methylthio]-ethyl}-N''-cyanoguanidine H are shown in the enclosed FIGS. 1 and 2 respectively.

The infrared examinations were accomplished in such a way that a sample of 1 mg was homogenized with 300 mg of KBr and pellets were prepared. The spectra were taken up with the pellets on a Nicolet 7000 FT-IR spectrophotometer. The X-ray diffraction studies were performed on a Zeiss HZG 4/c X-ray diffractometer. The exposures were made with Cu tube (40 kV, 20 mA, Ni filter) at a rate of 1°/min of the goniometer and at a rate of 1 cm/min of the paper. The characteristic bands and the lattice planes calculated on the basis of the X-ray diagrams are given in Example 1.

The investigation results of the X-ray diffractions of the known modifications B and C, which can be obtained from aqueous media, are different from case to case because of the amorphous appearance of the products. Oppositely, the modification H is in all cases identical concerning X-ray diffraction and can be prepared in a stable crystal form. The practical importance of the modification H consists in that it is a well-settling, sand-like precipitate which can be filtered rapidly, washed well and after suction or centrifugation, it contains not more than 30–35% of moisture.

As contrasted to the favourable properties of the modification H, the modification B is a precipitate with a large surface adsorbing a large amount of the solution and thus its dry substance content is 20 to 33% in a filter-wet state. The washing out and drying of this precipitate is not simple.

Further details of the invention are given in the following non-limiting Examples.

EXAMPLE 1

Preparation of N-methyl-N'-{2-[(5-methylimidazol-4-yl)-methylthio]-ethyl}-N''-cyanoguanidine H N-cyano-N'-{2-[(5-methylimidazol-4-yl)-methylthio]-ethyl}-S-methylisothiourea monohydrate (14.35 g; 0.05 mole) is suspended in distilled water (50 ml), stirred and heated. At a bath temperature of 50° C., aqueous methylamine solution (18.5 ml containing 411 g/liter of methylamine, i.e. 0.245 mole equal to 4.9 equivalents) is added. The evolving gas is led to an equipment for destruction (annihilation). The reaction mixture is kept in a bath of 50°–55° C. for 2.5 hours. Initially, the mixture becomes considerably thinner, then, in most cases, N-methyl-N'-{2-[(5-methylimidazol-4-yl)-methylthio]-ethyl}-N''-cyanoguanidine begins to precipitate without appearing of a complete solution. The mixture becomes thicker and eventually the stirring is stopped. After 2.5 hours the mixture is rapidly heated to 90° C. and stirred at this temperature for 30 minutes. The solution should not contain undissolved material. The solution is poured without cooling onto stirred ice (70 g). A clear solution of 0° to 10° C. is formed which becomes turbid and granular, and well-settling crystals separate. The solution is kept in a refrigerator for 2 hours, then filtered and washed with distilled water (2×10 ml). The wet weight of this precipitate is 14.8 g. After drying at 40° C., the dry weight of N-methyl-N'-{2-[(5-methylimidazol-4-yl)-methylthio]-ethyl}-N''-cyanoguanidine H is 12.27 g (90.82%); m.p. 73°–75° C.

The characteristic bands of the infrared spectrum are: 3502, 3388, 3302, 3042, 2940, 2153, 1594, 1573, 1369, 1258, 1061, 1000, 960, 723, 639, 478 cm$^{-1}$. It is further characteristic that no peak is observed at 1200 cm$^{-1}$; at 1180 cm$^{-1}$, where the most extensive sign is found with the aqueous modifications known so far, a very weak absorption can only be seen.

The values of distance of the X-ray diffraction lattic planes are: 5.861; 4.287; 4.168; 3.743; 3.689; 3.630; 3.424; 3.317; 3.328; 3.195; 3.150; 2.803; 3.724 R.

EXAMPLE 2

Preparation of N-methyl-N'-{2-[(5-methylimidazol-4-yl)-methylthio]-ethyl}-N''-cyanoguanidine H.

The substance (10 g) obtained according to Example 1 is dissolved in water (50 ml) and the hot solution is poured onto ice (75 g) while stirring to yield 9.85 g (98.5%) of N-methyl-N'-{2-[(5-methylimidazol-4-yl)-methylthio]-ethyl}-N''-cyanoguanidine H; m.p. 73° C.

On the basis of the Karl-Fischer's determination, its water content is 6.5% (the theoretical value is 6.67%). The N content found is 31.30% (calcd. 31.09%).

EXAMPLE 3

Preparation of N-methyl-N'-{2-[(5-methylimidazol-4-yl)-methylthio]-ethyl}-N''-cyanoguanidine A (a) N-methyl-N'-{2-[(5-methylimidazol-4-yl)-methylthio]-ethyl}-N''-cyanoguanidine H (23.5 g) is dissolved in isopropanol (100 ml), decolourized with carbon (0.5 g), filtered and set aside at −5° C. for 10 hours following the separation of the precipitate. After filtration 20.96 g (95.5%) of N-methyl-N'-{2-[(5-methylimidazol-4-yl)-methylthio]-ethyl}-N''-cyanoguanidine A are obtained.

(b) The filter-wet product obtained according to Example 1 (14.8 g containing 12.27 g of N-methyl-N'-{2-[(5-methylimidazol-4-yl)-methylthio]-ethyl}-N''-cyanoguanidine H) is dissolved in isopropanol (45 ml), decolourized with carbon, filtered and dried to give 10.52 g (91.86%) of N-methyl-N'-{2-[(5-methylimidazol-4-yl)-methylthio]-ethyl}-N''-cyanoguanidine A.

What we claim is:

1. N-methyl-N'-{2-[(5-methylimidazol-4-yl)-methylthio]-ethyl}-N''-cyanoguanidine monohydrate.

* * * * *